United States Patent [19]

Hednerson et al.

[11] Patent Number: 5,405,391
[45] Date of Patent: Apr. 11, 1995

[54] FUSION STABILIZATION CHAMBER

[76] Inventors: Fraser C. Hednerson; Rebecca S. Henderson, both of Upper Marlboro; John W. Newman, Berwyn, Pa.

[21] Appl. No.: 18,373

[22] Filed: Feb. 16, 1993

[51] Int. Cl.⁶ .............................................. A61F 2/44
[52] U.S. Cl. ....................................... 623/17; 606/61; 403/109
[58] Field of Search ................... 623/17, 16; 403/109; 606/61, 63, 72; 623/16

[56] References Cited

U.S. PATENT DOCUMENTS 5,290,312  3/1994  Kojimoto et al. ..................... 623/17

Primary Examiner—David H. Willse
Attorney, Agent, or Firm—William H. Eilberg

[57] ABSTRACT

A fusion stabilization chamber stabilizes the spine following removal of one or more vertebrae, and facilitates bone growth. The chamber includes two hollow members, preferably having slightly trapezoidal cross-sections, which slide relative to each other in a telescoping manner. The hollow members preferably have walls made of a metal mesh. Barrel vaults attached to the hollow members form guides for screws which can attach the chamber to the vertebrae adjacent the corpectomy site. Because of its adjustability, the chamber can fit a wide variety of corpectomy sites. One can fill the chamber with bone material, which can eventually fuse to the adjacent bone. A pair of stabilizing plates prevents the surgeon from pushing the chamber too far towards the spinal cord. The chamber eliminates the need to maintain a large and costly inventory of screws, and neurosurgeons can learn to use it quickly and easily.

13 Claims, 4 Drawing Sheets

FUSION STABILIZATION CHAMBER

BACKGROUND OF THE INVENTION

The present invention relates to the field of neurosurgery, and provides a device which facilitates the implantation of bone into the spine following removal of vertebrae, and which also facilitates the fusion of the implanted bone with the surrounding bone. The invention also includes a method of performing spinal surgery, and in particular, of stabilizing the spine following removal of one or more vertebrae.

Cancer or trauma or degenerative changes can cause parts of the human vertebrae to develop outgrowths or ridges that can touch the spinal cord and cause pain and/or paralysis. Neurosurgeons have developed means of treating such conditions, by removing part of the vertebrae, and, where appropriate, replacing the removed bone with something else. The removal of all or part of a vertebra is called a "corpectomy" or a "vertebrectomy". In some cases, one can replace the bone removed by corpectomy with bone taken from another site on the body of the patient; in other cases, one can obtain bone from a "bone bank". Given the right conditions, the new bone material will fuse to the bone surrounding the corpectomy site, and can become for practical purposes a part of the patient's body. To achieve the desired fusion, one must stabilize the spine so that the bone has time to fuse. The fusion process can take from six weeks to six months.

In performing spinal surgery, one can approach the spine either from the front (anterior) or rear (posterior) sides. The posterior approach has the disadvantage that since the vertebrae lie on the anterior side of the spinal cord, the surgeon must navigate past the spinal cord before reaching the vertebrae, and must take special care not to disturb the spinal cord. Conversely, with the anterior approach, the surgeon does not encounter the spinal cord while en route to the vertebrae. The present invention concerns the anterior approach.

The prior art contains many systems for stabilizing various parts of the spine following surgery. The development of such systems has made it possible to treat certain lesions of the spine aggressively, instead of simply immobilizing them in a brace. The typical external immobilizing device of the prior art comprises the halo vest. The typical internal immobilizing device comprises the Caspar plate, described below.

The Caspar plate system, named after Dr. Wolfhard Caspar, comprises a means for stabilizing the spine after anterior spinal surgery. The Caspar system includes a set of plates which one attaches to the remaining vertebrae surrounding the corpectomy site. In the Caspar procedure, one screws a plate directly onto the spine, the screws approaching within about one or two millimeters of the spinal cord. The Caspar system provides immediate stabilization of the spine following a corpectomy, and in other cases where the spine has become unstable following an accident. The Caspar system also eliminates the need for wearing the very cumbersome halo vest, and eliminates the need to undergo a separate surgical procedure from the rear.

However, the Caspar system also has disadvantages. It requires a large inventory of expensive equipment, including screws and plates of all sizes. The latter expense can represent a formidable obstacle to many medical institutions. Also, one needs to insert the screws through the spine, engaging the posterior cortex. Although one can monitor the position of the screws with an appropriate real-time viewing apparatus, the procedure carries the potential risk of spinal cord injury or laceration of the vertebral artery. When a competent surgeon performs the procedure, these complications rarely occur, but other complications such as loosening of the screws and persistent instability may develop. Moreover, the difficulty of the procedure discourages many surgeons from even attempting the anterior plating procedure.

The Synthes cervical spine locking plate constitutes another anterior plating system of the prior art. In the Synthes system, one inserts a second screw into the head of the anchor screw, thus creating a second affixation of the plate to the vertebrae. Many regard the Synthes system as easier, safer, and faster to use than the Caspar plate system, because the anchor screw does not penetrate the posterior cortex and because one therefore does not need to monitor the precise position of the screw during insertion. However, the Synthes locking plate has less versatility than the Caspar plate, as it provides the ability to fuse only two to three levels of the cervical spine.

Both the Caspar and Synthes systems also have the disadvantage that they do not work well in patients with osteoporosis, rheumatoid arthritis, ankylosing spondylitis, and other conditions of poor bone growth or metabolic bone disease.

Both the Caspar and Synthes systems have additional disadvantages inherent with the use of screws. First, as mentioned above, screws do become loose. If one uses the screws as the primary means of affixing the stabilizing device to the spine of the patient, loosening of the screws represents a major problem. Moreover, the use of screws presents a technical challenge to the surgeon. Correct screw placement requires experience, as well as a large inventory of expensive equipment, as well as imaging devices for monitoring the position of such screws. Also, with screw-based systems of the prior art, the surgeon must create a large opening in the patient, so as to view the screw along its shaft. Such an opening creates additional risks to the patient, such as the risk of injury to vascular structure and to nearby nerves.

In addition to the problem of how to stabilize the spine immediately after performing a corpectomy, vertebral surgery poses problems relating to the replacement of the removed bone. Some systems of the prior art require the use of a bone strut to replace the diseased bone segments removed in surgery. This bone grafting material costs a great deal, and sometimes one cannot obtain enough material when performing multiple vertebrectomies. Furthermore, bone graft material, usually taken from cadavers, has typically been sterilized by radiation, a process believed to weaken or destroy the strength and osteoconductive properties of bone. While it is possible to use other means of sterilization, such as ethylene oxide or freeze drying, it usually turns out that the best bone graft material comes from the patient, because the patient's own bone will likely fuse more rapidly than bone obtained elsewhere. Unfortunately, harvesting such bone consumes substantial time, involves substantial pain to the patient, and presents other risks, such as risk of infection at the harvest site, hemorrhage, and peripheral nerve injury.

The present invention overcomes the disadvantages of the prior art systems described above. First, the invention provides a device which surgeons can learn to use very easily, and which they can insert without intraoperative fluoroscopy or other means of accurately monitoring the position of a device within the body. Most neurosurgeons can use the device of the present invention with instruments already in their possession.

Secondly, the invention provides an adjustable device which can fit a large range of patients. This feature eliminates the need to keep a large inventory of parts in order to accommodate every possible patient.

Thirdly, the device allows one to use the patient's own cancellous bone which one removes during the vertebrectomy, possibly with the addition of further cancellous bone material from an external source. In any event, the invention reduces or eliminates the need to obtain a pelvic bone autograft from the patient.

The device of the present invention also reduces or eliminates the problem of loosening of screws, which can occur with the plating systems of the prior art, and which clearly can cause substantial pain and expense.

SUMMARY OF THE INVENTION

The fusion stabilization chamber of the present invention includes a pair of hollow members, both of which may have a rectangular or slightly trapezoidal cross-section. One of the hollow members slides within the other. Thus, the chamber comprises two telescoping hollow members. Each hollow member includes at least one barrel vault at one end, each barrel vault comprising threaded means for receiving a screw. The barrel vaults are arranged in a mutually oblique manner, such that the screws inserted into the vaults also lie along mutually oblique lines. The hollow members preferably comprise enclosures defined by four walls formed of a metal mesh. The hollow members may also include means for locking the members in a desired position relative to each other.

In using the stabilization chamber described above, the surgeon first removes the diseased portion of vertebra in the usual manner. The surgeon measures the length of the corpectomy site (the length of the space to be filled), and adjusts the length of the chamber accordingly. One may fasten the locking means so that the telescoping chamber maintains its desired position. Then, the surgeon fills the chamber with bone material, such as bone chips obtained from the corpectomy operation itself, or bone material from other sources, and inserts the chamber into the corpectomy site. The surgeon gently taps the device into place, so that it fills most of the corpectomy site, i.e. the space formerly occupied by the removed vertebra. The chamber does not extend all of the way towards the spinal cord, due to the retaining action of a pair of stabilizing plates.

The surgeon then drills holes in the surrounding bone, using the barrel vaults as guides for the drill bit. The surgeon then inserts the screws through the barrel vaults and fastens them to the bone. Due to the orientation of the barrel vaults, the screws lie along mutually oblique paths, reducing the likelihood that the device will become dislodged.

In an alternative embodiment, one can provide threaded holes in the stabilizing plates also, so that additional screws can pass directly through the stabilizing plates and into the surrounding bone.

The present invention therefore has the primary object of providing an improved method and apparatus for performing spinal surgery, and in particular, for stabilizing the spine following removal of one or more vertebrae.

The invention has the further object of providing a device which promotes bone fusion in addition to providing stabilization of the spine.

The invention has the further object of simplifying the surgical process of stabilizing the spine after performing a corpectomy.

The invention has the further object of reducing the cost and complexity of the equipment needed to practice spinal surgery.

The invention has the further object of reducing the time required for a surgeon to learn to stabilize the spine following a corpectomy.

Persons skilled in the art will recognize other objects and advantages of the invention, from a reading of the following brief description of the drawings, the detailed description of the invention, and the appended claims.

DETAILED DESCRIPTION OF THE INVENTION

Figure 1:
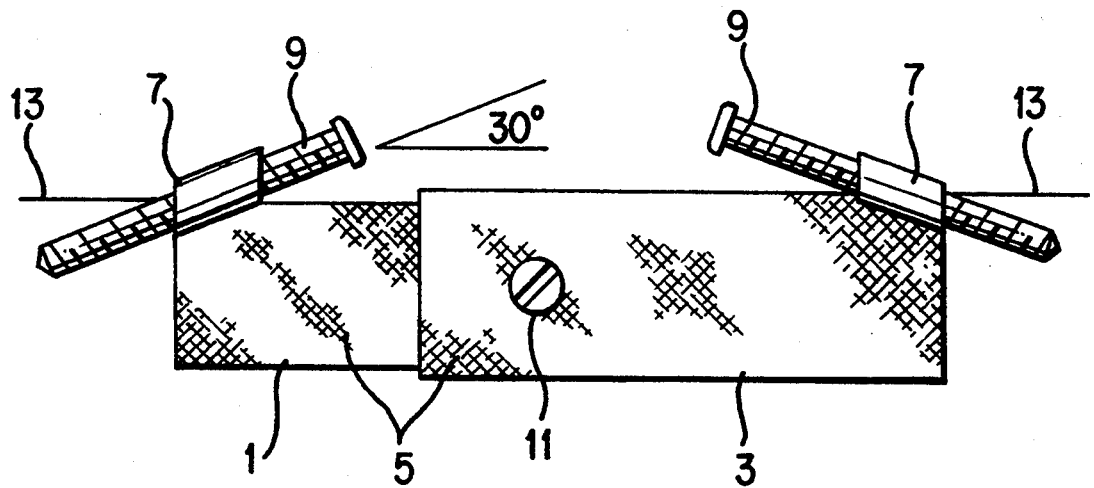
FIG. 1 provides a side elevational view of the fusion stabilization chamber of the present invention.
Figure 2:
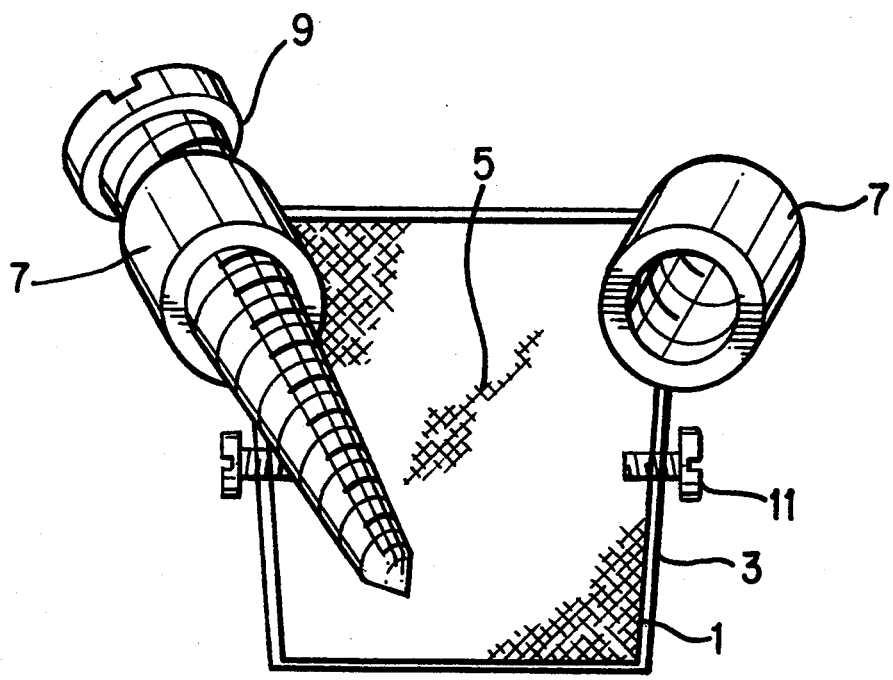
FIG. 2 shows an end view of the stabilization chamber of the present invention.
Figure 3:
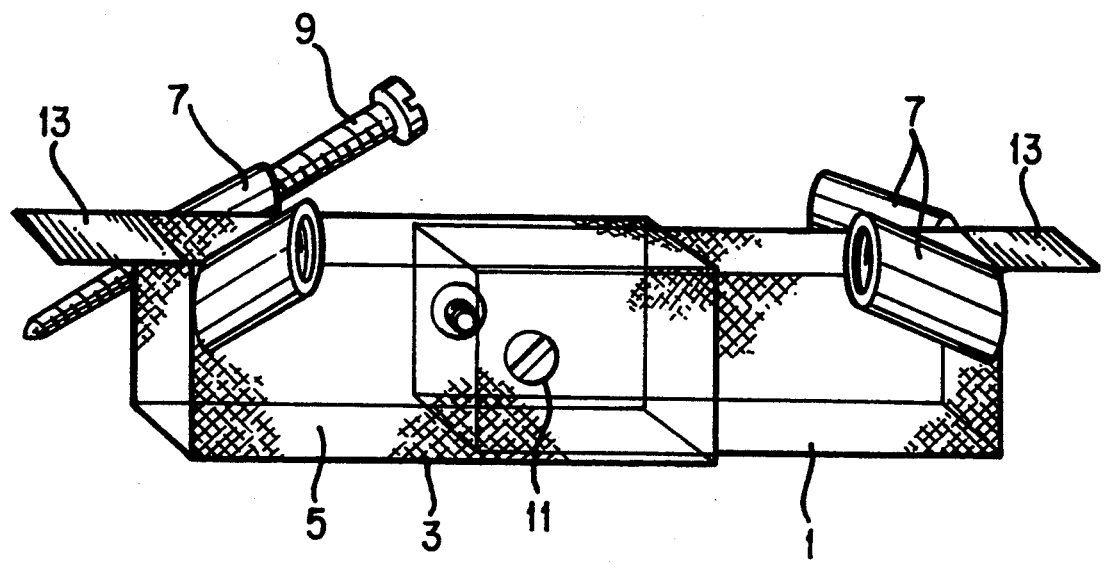
FIG. 3 provides a perspective view of the fusion stabilization chamber.

FIGS. 1–4 show the physical structure of the fusion stabilization chamber of the present invention. The chamber includes first hollow member 1 and second hollow member 3. Both hollow members have a slightly trapezoidal cross-section, as illustrated in the end view of FIG. 2. FIG. 2 exaggerates the trapezoidal shape of the cross-section; in practice, the width of the member might increase by one millimeter for each 15 mm of depth, but one could use other dimensions. Thus, by "slightly trapezoidal", one means that the members are nearly rectangular in cross-section, except for the variation in width described above. The trapezoidal cross-section helps to maintain the chamber in position within the corpectomy site. One inserts the narrower portion of the hollow member into the body cavity first, with the wider portion oriented towards the outside. Thus, the chamber tends to become wedged in its place within the corpectomy site; once pushed in, it becomes difficult to pull out. Although the preferred embodiment includes the trapezoidal cross-section, one can also form the chamber with a perfectly rectangular cross-section, within the scope of the invention.

The first hollow member 1 slides within the second hollow member 3. The members 1 and 3 preferably have walls formed of metal mesh 5. One prefers walls having openings which permit bone growth from the adjacent vertebrae, through the interior of the chamber. However, the walls can have a different construction. They can even comprise solid metal, as bone can fuse to metal. In the latter case, the chamber could be empty.

Figure 4:
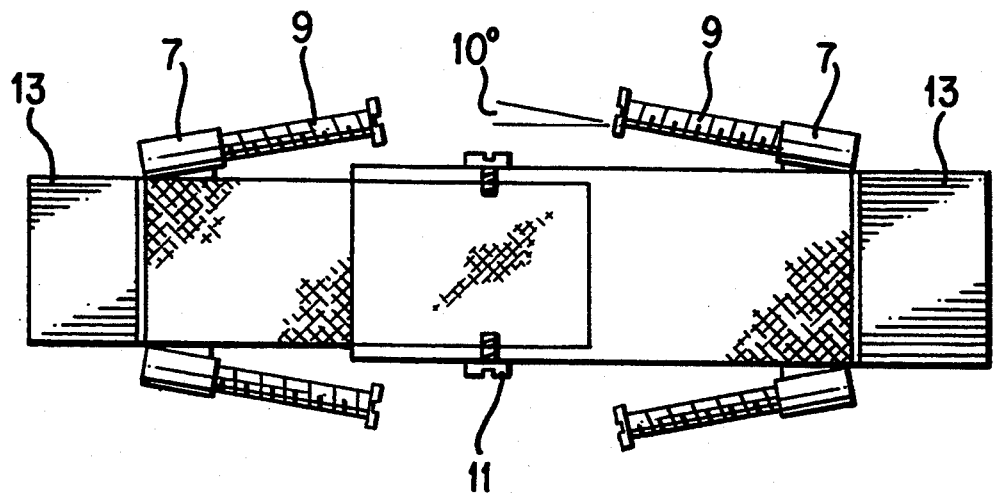
FIG. 4 shows a top view of the stabilization chamber.

In the preferred embodiment, the chamber has two pairs of barrel vaults 7, arranged at the opposite ends of the hollow members. One can vary the number of barrel vaults, within the scope of the invention. The barrel vaults comprise threaded cylinders through which screws 9 pass. FIG. 1 shows that the screws form an angle of about 30° relative to the top longitudinal axis of the chamber. FIG. 4 shows that the screws also form an angle of about 10° relative to the sides of the chamber. One can vary these angles; one should not consider the invention limited to particular angles. In general, one selects angles which enable the screws to pass through the greatest possible thickness of bone, above and below the corpectomy site, and to provide an angle which, from the perspective of the surgeon, facilitates insertion of the screws without the need to make a larger or additional incision.

As shown in the Figures, the barrel vaults comprise mutually oblique members. The screws become self-locking in the barrel vaults. One can also provide an adjustable hexagonal head screwdriver to facilitate tightening of the screws from any angle.

Locking screw 11 holds the first and second hollow members in place. The locking screw thus permits adjustment of the size of the chamber. One slides the hollow members until the chamber has the desired length, and then fixes the selected length by tightening the locking screw.

Figure 5:
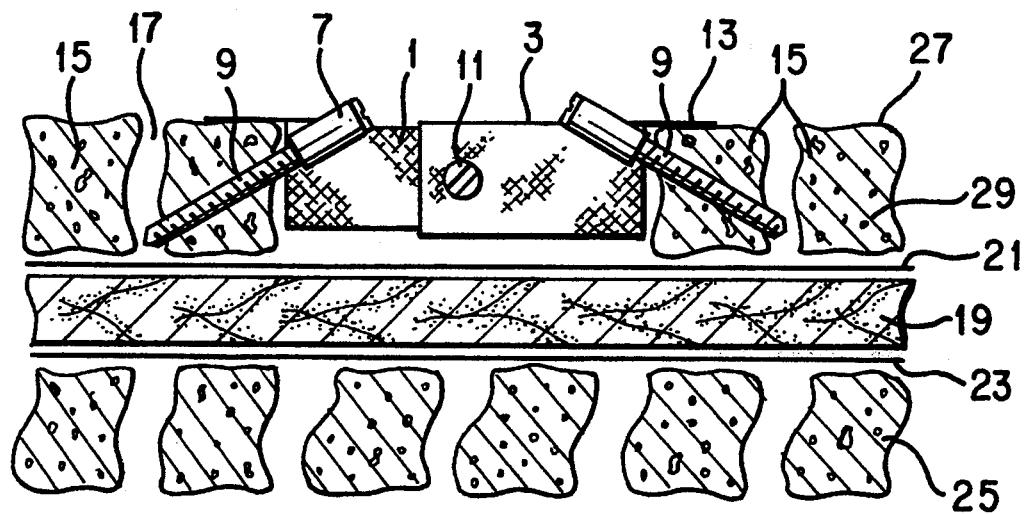
FIG. 5 provides a diagrammatic view showing the fusion stabilization chamber inserted into a corpectomy site.

FIG. 5 provides a diagram of the fusion stabilization chamber inserted into a corpectomy site. The figure shows vertebrae 15, the spaces 17 between adjacent vertebrae representing intervertebral discs. Each vertebra includes an outer bony layer, or cortex 27, which surrounds cancellous material 29 inside. FIG. 5 also shows spinal cord 19, and the structures adjoining the spinal cord, including the posterior longitudinal ligament 21, the ligamentum flavum 23, and the posterior spinous processes 25. As shown in the figure, one has removed several vertebrae, and has inserted the chamber into the resulting empty space.

Stabilizing plates 13 extend from both hollow members, as shown in the Figures. The stabilizing plates serve several purposes. First, as illustrated in FIG. 5, the stabilizing plates keep the chamber at an appropriate depth, preventing the chamber from touching spinal cord 19 or the ligaments surrounding it. By making the depth of the chamber less than the depth of the adjacent vertebrae, one prevents the chamber from coming too close to the spinal cord.

Secondly, the stabilizing plates tend to distribute the bending loads experienced by the chamber, and divert part of these loads away from the screws. As the vertebrae flex back and forth, the stabilizing plates tend to oppose some of the vertebral movement, and absorb some of the tension, thereby tending to prevent the screws from loosening or breaking.

Thirdly, the stabilizing plates help to rigidify the joints formed between the ends of the chamber and the respective adjacent vertebrae. Keeping these joints rigid facilitates the growth of blood vessels from the adjacent vertebrae, through the holes in the chamber walls, and into the bone material within the chamber.

Figure 6:
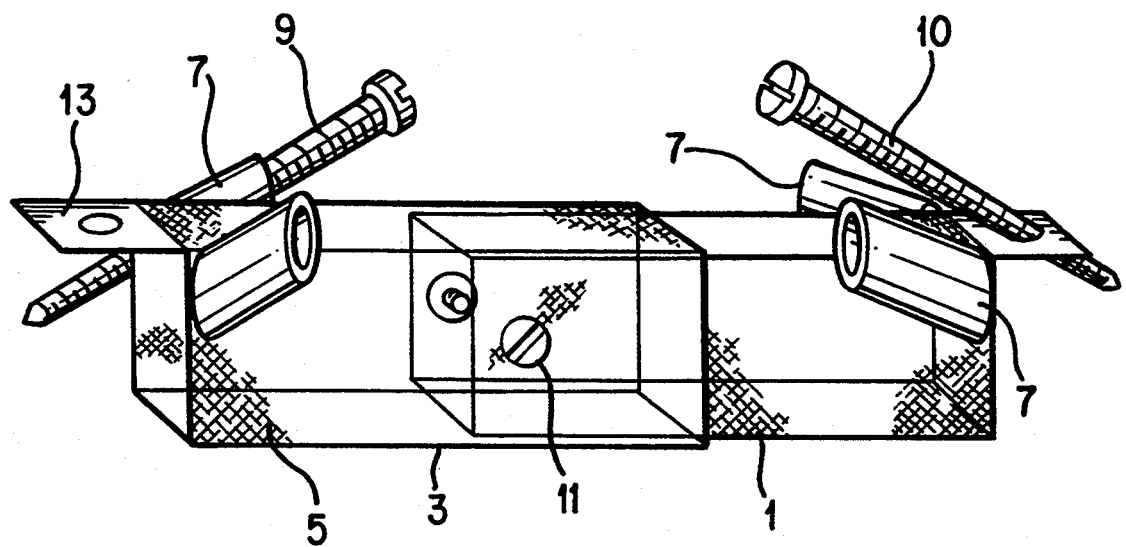
FIG. 6 provides a perspective view of an alternative embodiment of the invention, wherein additional screws pass directly through the stabilizing plates.

FIG. 6 shows, in a perspective view, an alternative embodiment wherein a third screw passes through a threaded hole in each stabilizing plate, in addition to the pair of screws inserted through the associated barrel vaults. FIG. 6 shows additional screw 10 inserted through the stabilizing plate on the right-hand side. The figure does not show the corresponding additional screw on the other side, in order to show the hole in the stabilizing plate, but in practice a similar additional screw 10 would normally be provided. However, one should consider each screw as optional, since it is possible to affix the chamber to the adjacent bone using fewer than all of the available screws.

One would use the embodiment of FIG. 6 in cases where the bone has become weakened. In rare cases, one might even attach the chamber only with the stabilizing plate screws, without any barrel vault screws. In all of the embodiments wherein one provides a threaded hole in the stabilizing plate, the holes should have low "profiles", so that the material defining the plate does not project significantly beyond the plane of the plate.

In using the chamber of the present invention, the surgeon begins by performing a corpectomy in the conventional manner. Immediately after removal of one or more vertebrae, the surgeon measures the length of the corpectomy site with calipers, and adjusts the length of the chamber to make it conform to the length of the corpectomy site. One adjusts the length of the chamber by pulling the hollow members 1 and 3 away from each other or pushing them together, as needed. Then one tightens the locking screw 11 to fix the length (and thus the volume) of the chamber.

Next, the surgeon fills the chamber with bone. The bone can comprise bone chips obtained from the vertebrae removed in the corpectomy procedure, or it can comprise cancellous bone obtained from another site. One might also use a biocompatible osteogenic polymer.

In a variation of the latter step, the surgeon may place bone chips, obtained from the corpectomy, into the chamber, while the corpectomy progresses. However, in this case, one would still need to adjust the chamber to fit the corpectomy site, and one would also need to insure that the bone has substantially filled the volume of the chamber after adjustment of the size of the chamber.

The surgeon then inserts the bone-filled chamber into the corpectomy site, and gently taps it into place, such that the stabilization plates 13 come to rest on the vertebrae immediately adjacent to the corpectomy site. The chamber should fit tightly within the corpectomy site. One may take a lateral spine X-ray to insure that the chamber has seated itself properly in the corpectomy site.

Next, the surgeon drills holes into the adjacent vertebrae, using an appropriate drill, such as a 2 mm twist drill. The barrel vaults 7 form guides for the drill bit, and thereby determine the direction of the holes. The orientation of the barrel vaults unambiguously determines the orientation of the holes. The holes therefore make the same angles as the barrel vaults, relative to the axes of the chamber.

The surgeon then threads the screws 9 into the barrel vaults 7. The barrel vaults direct the screws along the correct path. Due to the interaction of the heads of screws 9 with the barrel vaults, the barrel vaults also insure that the screws 9 become inserted to the correct depth. When tightened, the screws 9 tend to draw the adjacent vertebrae towards the chamber. Note also that the screws pass twice through the cortex of the vertebrae. In other words, each screw has a length sufficient to pass through the cortex 27 at one surface of the vertebra, then through the cancellous material 29 at the core of the vertebra, and again through the cortex as the screw exits the vertebra. Fastening the screws in this manner minimizes the likelihood that the screws will become dislodged.

Following the tightening of the screws, one can take a lateral X-ray to verify proper placement of the screws. If all is correct, one can then close the wound in the conventional manner.

The present invention has many advantages, as outlined below:

1. The fusion stabilization chamber does not rely on screws as the sole means of stabilizing the spine following surgery. Due to the trapezoidal cross-section of the chamber, the chamber becomes firmly wedged within the corpectomy site even before attachment of the screws.
2. The surgeon can learn to insert the fusion stabilization chamber much more quickly than devices of the prior art. Since the barrel vaults automatically determine the direction and depth of the screws, the surgeon will be less likely to make mistakes while using the present invention, and the invention therefore is less intimidating to the surgeon than devices of the prior art. In particular, the oblique direction of the screws lessens the potential damage to the spinal cord. Moreover, most neurosurgeons can use the fusion stabilization chamber with instruments already in their possession.
3. The oblique direction of the screws has the added benefit that it increases the compression effect, by drawing vertebrae above and below the chamber into firm contact with the chamber. Such compression speeds fusion of the bone.
4. The oblique direction of the screws has the additional advantage of reducing the required size of the surgical incision, because the surgeon can reach deeply into adjacent vertebrae, using the screws, without exposing those vertebrae.
5. Because of the ease and manner of insertion of the device, the surgeon need not use intraoperative fluoroscopy, or other monitoring means, while inserting the device.
6. The present invention eliminates the need for a large inventory of stabilization plates and screws for fitting different sizes of vertebrae. One can construct the present invention in two or three basic sizes, which together fit virtually all possible corpectomy sites, due to the telescoping feature of the chamber. Thus, the invention reduces the cost of maintaining an inventory of materials. Moreover, due to the simple structure of the fusion stabilization chamber, one can manufacture it relatively inexpensively.
7. One can make the fusion stabilization chamber of strong titanium metal mesh which allows bone to grow from end to end and from side to side. One can easily fill the chamber with the patient's own cancellous bone mixed with hydroxyapatite crystals and/or other biocompatible synthetic bone substitutes known to increase the rate of bone formation. Thus, the present invention reduces the need to harvest bone from other sites on the patient's body.
8. The structure of the fusion stabilization chamber provides stability through all three degrees of freedom of movement.

In an alternative embodiment, one can replace the locking screw with a screw device located inside the chamber and extending along the entire length of the chamber. Thus, the latter screw device would comprise a type of jack. Turning the latter screw would vary the overall length of the jack, which is equivalent to varying the length of the chamber. With this arrangement, one need not adjust the length of the chamber before inserting it into the corpectomy site. Instead, one would first insert the chamber, and then turn the screw to adjust the jack, until the chamber becomes long enough to occupy the entire space. The above-described screw device would then comprise the means for locking the hollow members into a fixed position relative to each other, and could be used instead of, or in addition to, locking screw 11. One would use a bevel gear, or equivalent mechanical device, for adjusting the jack while the chamber is in position. The latter alternative should be considered within the scope of the present invention.

In another alternative embodiment, one can coat the outside of the chamber with an osteoconductive substance, such as hydroxyapatite, or the like, to promote fusion of the chamber to the surrounding bone. This coating can be instead of, or in addition to, the filling of the chamber with bone material. The invention should be considered to include the latter alternatives.

The chamber used in the present invention can have various cross-sections. The invention is not limited to the rectangular or trapezoidal cross-sections discussed above, but can include other shapes. For example, one could form the chamber with a circular cross-section, in which case the chamber would have the general shape of a cylinder.

Figure 7:
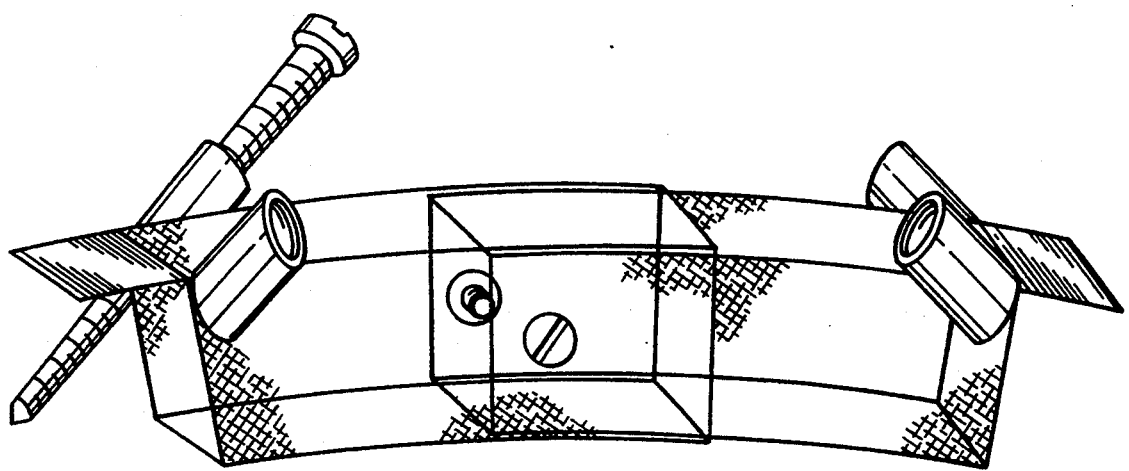
FIG. 7 provides a perspective view, similar to that of FIG. 3, showing an embodiment in which the fusion stabilization chamber is curved to fit the curvature of the spine.

The present invention is also not limited to a chamber having straight walls. Instead, the chamber could be curved along its length as shown in FIG. 7. In this way, one can make the chamber fit the curvature of the spine. In the latter case, both hollow members would be curved, so that they could slide back and forth within each other, while maintaining the desired curvature. This embodiment would be useful for a corpectomy which spans a relatively large number of vertebrae.

While the above description illustrates the preferred embodiments of the invention, one can vary the invention in still other ways. For example, as noted above, one can vary the structure of the walls of the chamber. While one prefers a chamber having holes, such as provided by a metal mesh, one could use an empty box having solid walls. The position and number of barrel vaults can also vary. These and other modifications, which those skilled in the art will recognize, should be considered within the spirit and scope of the following claims.

What is claimed is:

1. A fusion stabilization chamber, comprising:
   a) first and second hollow members, the first hollow member being slidable within the second hollow member,
   b) both hollow members including at least one barrel vault for receiving a screw therein, at least one barrel vault of the first hollow member being mutually oblique to at least one barrel vault of the second hollow member, the hollow members being substantially filled with bone chips,
   c) wherein each hollow member is defined by walls formed of a metal mesh, the mesh defining openings sufficiently large to allow the bone chips located within the hollow member to fuse with bone material located outside the hollow member.

2. The fusion stabilization chamber of claim 1, wherein each barrel vault includes a screw threaded therein.

3. The fusion stabilization chamber of claim 1, further comprising means for locking the two hollow members in a position such that the hollow members together define a predetermined volume.

4. The fusion stabilization chamber of claim 1, wherein each hollow member is attached to a stabilizing plate, the stabilizing plates lying in generally the same plane, each stabilizing plate extending longitudinally outward from the hollow member.

5. The fusion stabilization chamber of claim 4, wherein at least one stabilizing plate has a threaded hole, and a screw inserted through said threaded hole.

6. The fusion stabilization chamber of claim 5, wherein each barrel vault includes a screw threaded therein.

7. The fusion stabilization chamber of claim 1, wherein the hollow members have a slightly trapezoidal cross-section.

8. A fusion stabilization chamber, comprising:
a) first and second hollow members, the first hollow member being slidable within the second hollow member, the hollow members having a slightly trapezoidal cross-section, the hollow members being substantially filled with bone chips,
b) both hollow members including at least two threaded barrel vaults with screws threaded in the barrel vaults, the barrel vaults of the first hollow being oblique to the barrel vaults of the second hollow member,
c) the hollow members being formed generally of a metal mesh, and
d) means for locking the two hollow members in a position such that the hollow members together define a predetermined volume.

9. The fusion stabilization chamber of claim 8, wherein each hollow member is attached to a stabilizing plate, the stabilizing plates lying in generally the same plane, each stabilizing plate extending longitudinally outward from the hollow member.

10. The fusion stabilization chamber of claim 9, wherein the stabilizing plates have threaded holes, and wherein there are screws inserted through said threaded holes.

11. A fusion stabilization chamber, comprising:
a) first and second hollow members, the first member being movable with respect to the second member, both hollow members being substantially filled with bone chips, wherein substantially all of each hollow member is formed of a metal mesh, the mesh defining openings sufficiently large to allow the bone chips located within the hollow member to fuse with bone material located outside the hollow member, the fusion stabilization chamber also including means for fixing the first and second members in a desired position relative to each other, and
b) means, attached to the first and second members, for affixing said first and second members to vertebrae adjacent a corpectomy site.

12. A fusion stabilization chamber, comprising:
a) first and second hollow members, the first hollow member being slidable within the second hollow member, the hollow members both having longitudinal axes, the hollow members being curved along their longitudinal axes, wherein the fusion stabilization chamber has a curvature which corresponds to a curvature of a patient's spine,
b) both hollow members including at least one barrel vault for receiving a screw therein, at least one barrel vault of the first hollow member being mutually oblique to at least one barrel vault of the second hollow member, the hollow members being substantially filled with bone chips,
c) wherein each hollow member is defined by walls formed of a metal mesh, the mesh defining openings sufficiently large to allow the bone chips located within the hollow member to fuse with bone material located outside the hollow member.

13. A fusion stabilization chamber, comprising:
a) first and second hollow members, the first member being movable with respect to the second member, both hollow members being substantially filled with bone chips, wherein substantially all of each hollow member is formed of a metal mesh, the mesh defining openings sufficiently large to allow the bone chips located within the hollow member to fuse with bone material located outside the hollow member, the fusion stabilization chamber also including means for fixing the first and second members in a desired position relative to each other, and
b) means, attached to the first and second members, for affixing said first and second members to vertebrae adjacent a corpectomy site,
wherein both hollow members have longitudinal axes, the hollow members being curved along their longitudinal axes, wherein the fusion stabilization chamber has a curvature which corresponds to a curvature of a patient's spine.

* * * * *

UNITED STATES PATENT AND TRADEMARK OFFICE
CERTIFICATE OF CORRECTION

PATENT NO. : 5,405,391
DATED : April 11, 1995
INVENTOR(S) : Fraser C. Henderson et al It is certified that error appears in the above-identified patent and that said Letters Patent is hereby corrected as shown below:

On the title page: Item [76] first inventor -- Henderson --

Signed and Sealed this

Twenty-second Day of August, 2000

Attest:

Q. TODD DICKINSON

*Attesting Officer*  *Director of Patents and Trademarks*